US012622735B2

(12) United States Patent
Wilms et al.

(10) Patent No.: US 12,622,735 B2
(45) Date of Patent: May 12, 2026

(54) SYSTEMS AND METHODS OF AN ELECTROHEMOSTATIC RENAL SHEATH

(71) Applicant: C. R. Bard, Inc., Murray Hill, NJ (US)

(72) Inventors: Abigail Wilms, Mason, OH (US); Dahoney L. Swarns, Covington, GA (US); Kevin Knollman, Mason, OH (US); Morgan Rex, Covington, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 661 days.

(21) Appl. No.: 15/966,739

(22) Filed: Apr. 30, 2018

(65) Prior Publication Data

US 2018/0317995 A1     Nov. 8, 2018

Related U.S. Application Data

(60) Provisional application No. 62/500,382, filed on May 2, 2017.

(51) Int. Cl.
*A61B 18/08*     (2006.01)
*A61B 18/12*     (2006.01)
(Continued)

(52) U.S. Cl.
CPC ........ *A61B 18/082* (2013.01); *A61B 18/1206* (2013.01); *A61B 18/1482* (2013.01);
(Continued)

(58) Field of Classification Search
CPC ............... A61F 7/12; A61F 2007/0288; A61B 18/082; A61B 2018/00005;
(Continued)

(56) References Cited

U.S. PATENT DOCUMENTS 5,098,431 A      3/1992 Rydell
5,928,163 A *    7/1999 Roberts .............. A61B 18/1445
                                                      600/567

(Continued)

FOREIGN PATENT DOCUMENTS

EP          2783651 A1    10/2014

OTHER PUBLICATIONS

Yeong-Chin, Electrocauterization of bleeding points for percutaneous nephrolithotomy, published 2004, Urology, 64 (3), 443-446 (Year: 2004).*

(Continued)

*Primary Examiner* — Kaitlyn E Smith
*Assistant Examiner* — Yasamin Ekrami
(74) *Attorney, Agent, or Firm* — Rutan & Tucker LLP

(57)     ABSTRACT

Systems and methods directed to a renal sheath, one or more electrode pairs in the renal sheath, and a wiring system configured to connect the one or more electrode pairs to an electric current. The renal sheath can include a distal end portion, a proximal end portion, and a medial portion between the distal and proximal end portions. The medial portion can include the one or more electrode pairs. The one or more electrode pairs can be configured to produce heat sufficient to induce hemostasis in bleeding tissue surrounding the renal sheath. The wiring system can be configured to connect the one or more electrode pairs to the electric current to produce the heat sufficient to effect the hemostasis. In some embodiments, an electrosurgical generator can be configured to provide an alternating current to the one or more electrode pairs to produce the heat sufficient to effect the hemostasis.

8 Claims, 5 Drawing Sheets

Figure 1A:
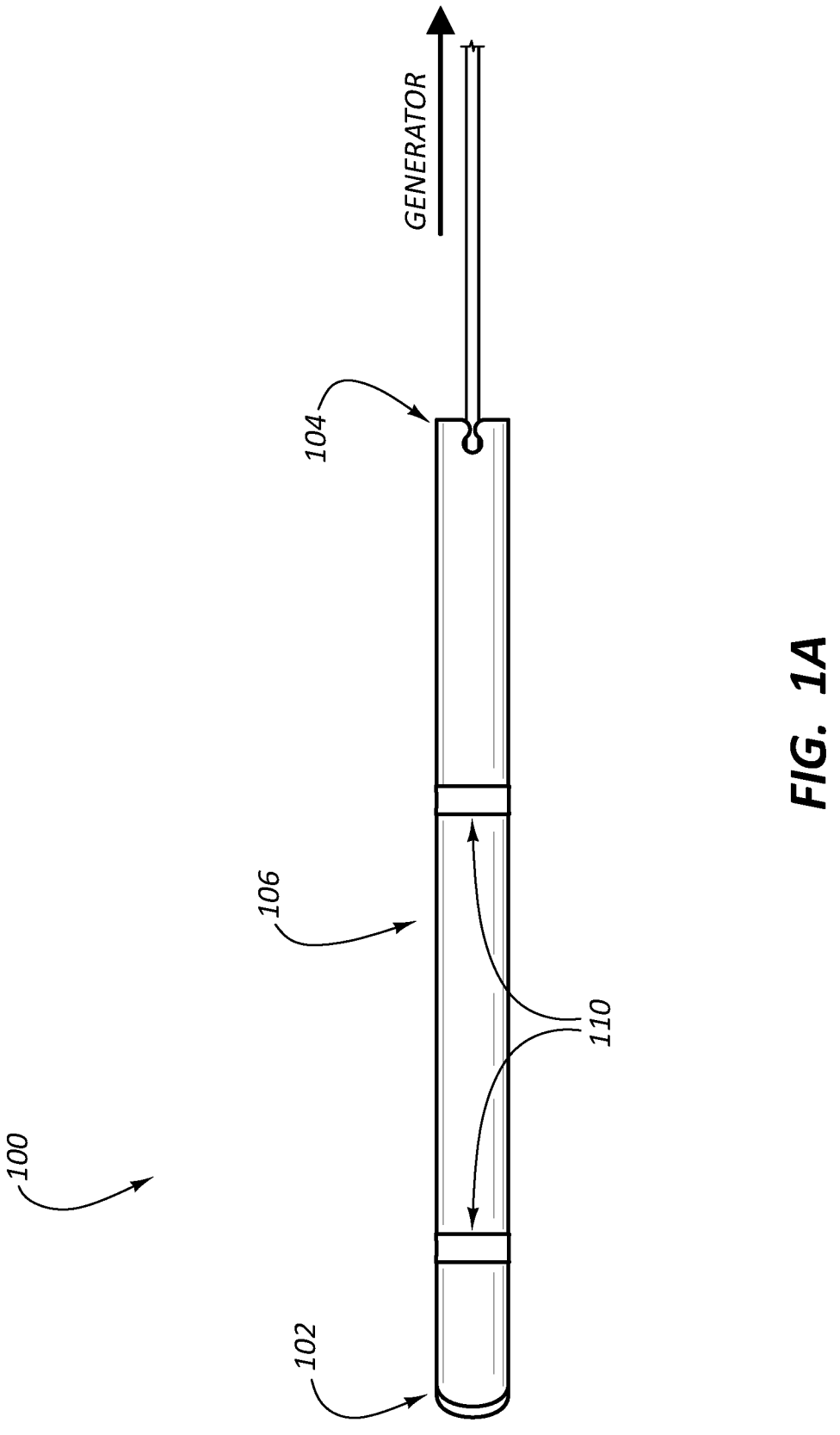

(51) Int. Cl.

| | |
|---|---|
| *A61B 18/14* | (2006.01) |
| *A61F 7/12* | (2006.01) |
| *A61B 17/12* | (2006.01) |
| *A61B 18/00* | (2006.01) |
| *A61B 90/00* | (2016.01) |
| *A61F 7/02* | (2006.01) |

(52) U.S. Cl.

CPC ...... *A61F 7/12* (2013.01); *A61B 2017/12004* (2013.01); *A61B 2018/00005* (2013.01); *A61B 2018/00511* (2013.01); *A61B 2018/00589* (2013.01); *A61B 2018/126* (2013.01); *A61B 2090/3937* (2016.02); *A61F 2007/0288* (2013.01)

(58) Field of Classification Search

CPC ........... A61B 2017/12004; A61B 2017/00721; A61B 2090/3937; A61B 2018/126; A61B 2018/00511; A61M 2210/1082

See application file for complete search history.

(56) References Cited

U.S. PATENT DOCUMENTS

| | | | | |
|---|---|---|---|---|
| 7,811,282 | B2 * | 10/2010 | McClurken | ........ A61B 18/1402 606/49 |
| 8,366,615 | B2 | 2/2013 | Razavi | |
| 8,709,039 | B2 | 4/2014 | Humphreys | |
| 2003/0091967 | A1 * | 5/2003 | Chosack | .............. G09B 23/285 434/262 |
| 2005/0065509 | A1 * | 3/2005 | Coldwell | ........... A61B 18/1477 606/41 |
| 2006/0025760 | A1 * | 2/2006 | Podhajsky | ......... A61B 18/1402 606/38 |
| 2006/0111704 | A1 * | 5/2006 | Brenneman | ........ A61B 18/1492 606/41 |
| 2008/0021486 | A1 * | 1/2008 | Oyola | ................ A61B 17/3211 606/169 |
| 2010/0174170 | A1 * | 7/2010 | Razavi | .............. A61M 25/0662 600/371 |
| 2010/0292764 | A1 | 11/2010 | Soomro et al. | |
| 2010/0298634 | A1 * | 11/2010 | Yanuma | ................. A61B 17/22 600/104 |
| 2011/0098704 | A1 * | 4/2011 | Long | ...................... A61B 90/08 606/45 |
| 2012/0303015 | A1 * | 11/2012 | Shin | ................... A61B 18/1477 606/33 |
| 2013/0211415 | A1 * | 8/2013 | Zerfas | .............. A61B 17/00234 606/1 |
| 2013/0304052 | A1 * | 11/2013 | Rizq | ...................... A61B 18/18 606/33 |
| 2016/0193449 | A1 * | 7/2016 | Sarabia | ............. A61M 25/0147 604/95.04 |
| 2017/0215964 | A1 * | 8/2017 | Harrah | ................. A61B 18/245 |

OTHER PUBLICATIONS

The American Heritage Dictionary, 2nd College Edition, p. 174 (1982).*

The American Heritage Dictionary, 2nd College Edition, p. 781 (1982).*

* cited by examiner

CURRENT THROUGH SHEATH-SURROUNDING TISSUE BETWEEN ACTIVE AND RETURN ELECTRODES PRODUCES HEMOSTASIS-INDUCING HEAT

SYSTEMS AND METHODS OF AN ELECTROHEMOSTATIC RENAL SHEATH

CROSS-REFERENCE

This application claims the benefit of priority of U.S. Provisional Application No. 62/500,382, filed May 2, 2017, which is hereby incorporated by reference in its entirety into this application.

BACKGROUND

Percutaneous nephrolithotomy ("PCNL") is a minimally invasive surgical procedure primarily for removing kidney stones or other kidney obstructions from kidneys, wherein the stones or the other obstructions are either too large or too complex to be removed by other procedures. In a PCNL procedure, a puncture is made with a needle through a patient's back and into a kidney. Once a tract is established by the needle, the needle is replaced by a guidewire, a dilator is advanced over the guidewire to dilate the tract, and a renal sheath is advanced over the dilator. Removal of the dilator leaves the renal sheath, which provides a portal through which the PCNL procedure can be completed. However, the PCNL procedure is not without complications such as patient bleeding. As such, the PCNL procedure can benefit from mitigating or eliminating complications such as patient bleeding. Provided herein in some embodiments are systems and methods that address the foregoing, thereby reducing risk associated with the PCNL procedure.

SUMMARY

Provided herein, in some embodiments, is a system including a renal sheath, one or more electrode pairs in the renal sheath, and a wiring system configured to connect the one or more electrode pairs to an electric current. The renal sheath can include a distal end portion, a proximal end portion, and a medial portion between the distal and proximal end portions, the medial portion including the one or more electrode pairs disposed therein. The one or more electrode pairs can be configured to produce heat sufficient to induce hemostasis in bleeding tissue surrounding the renal sheath. The wiring system can be configured to connect the one or more electrode pairs to the electric current to produce the heat sufficient to effect the hemostasis.

Also provided herein, in some embodiments, is a system including a renal sheath, one or more electrode pairs in the renal sheath, a wiring system configured to connect the one or more electrode pairs to an alternating electric current, and an electrosurgical generator configured to provide the alternating electric current. The renal sheath can include a distal end portion, a proximal end portion, and a medial portion between the distal and proximal end portions, the medial portion including the one or more electrode pairs disposed therein. The one or more electrode pairs can be configured to produce heat sufficient to induce hemostasis in bleeding tissue surrounding the renal sheath. The wiring system can be configured to connect the one or more electrode pairs to the electrosurgical generator-provided alternating electric current to produce the heat sufficient to effect the hemostasis.

Also provided herein, in some embodiments, is a system including a renal sheath, at least two electrode pairs embedded in the renal sheath, and a wiring system configured to connect the at least two electrode pairs to an alternating electric current. The renal sheath can include a distal end portion, a proximal end portion, and a medial portion between the distal and proximal end portions, the medial portion including the at least two electrode pairs embedded therein. Each electrode pair of the at least two electrode pairs can include an active electrode and a return electrode. The at least two electrode pairs can be configured to produce heat sufficient to induce hemostasis in circuit-completing bleeding tissue surrounding the renal sheath between the active and return electrodes. The wiring system can be configured to connect the at least two electrode pairs to the alternating electric current to produce the heat sufficient to effect the hemostasis. The wiring system can include a pair of wires at least partially disposed within a wall of the renal sheath extending from a proximal end of the renal sheath to a first electrode pair of the at least two electrode pairs. The wiring system can further include an external cable including an external portion of the pair of wires extending from the proximal end of the renal sheath. The wiring system can further include a connector at a proximal end of the external cable opposite the renal sheath configured to connect the renal sheath to an electrosurgical generator.

These and other features of the concepts provided herein may be better understood with reference to the drawings, description, and appended claims.

DRAWINGS

FIG. 1A provides a schematic illustrating a top view of a renal sheath with one or more electrode pairs in accordance with some embodiments.

Figure 1B:
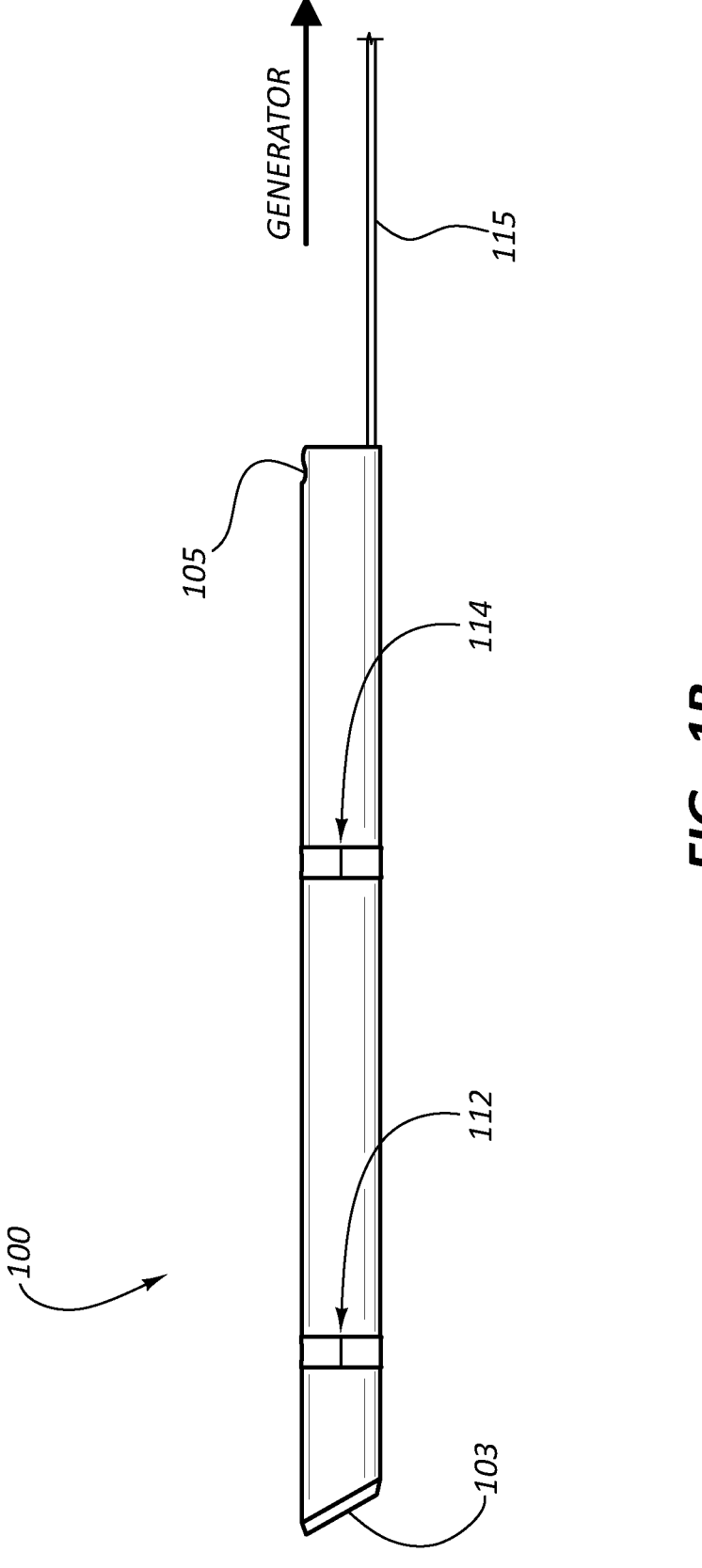

FIG. 1B provides a schematic illustrating a side view of a renal sheath with one or more electrode pairs in accordance with some embodiments.

Figure 2A:
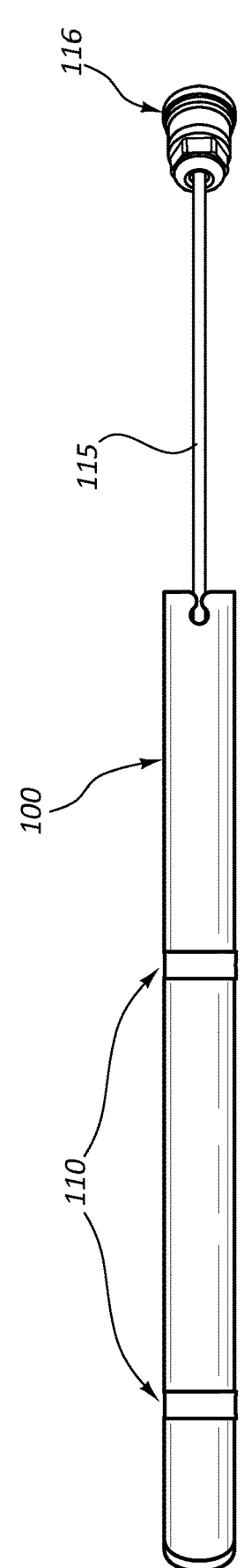

FIG. 2A provides a schematic illustrating a top view of a renal sheath with one or more electrode pairs in accordance with some embodiments.

Figure 2B:
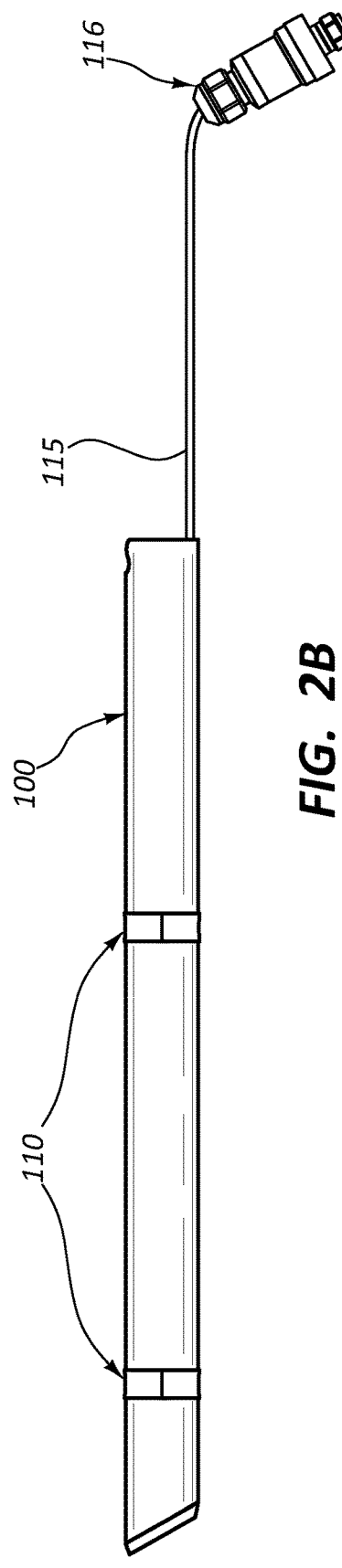

FIG. 2B provides a schematic illustrating a side view of a renal sheath with one or more electrode pairs in accordance with some embodiments.

Figure 2C:

FIG. 2C provides a schematic illustrating a perspective view of a renal sheath with one or more electrode pairs in accordance with some embodiments.

Figure 3:
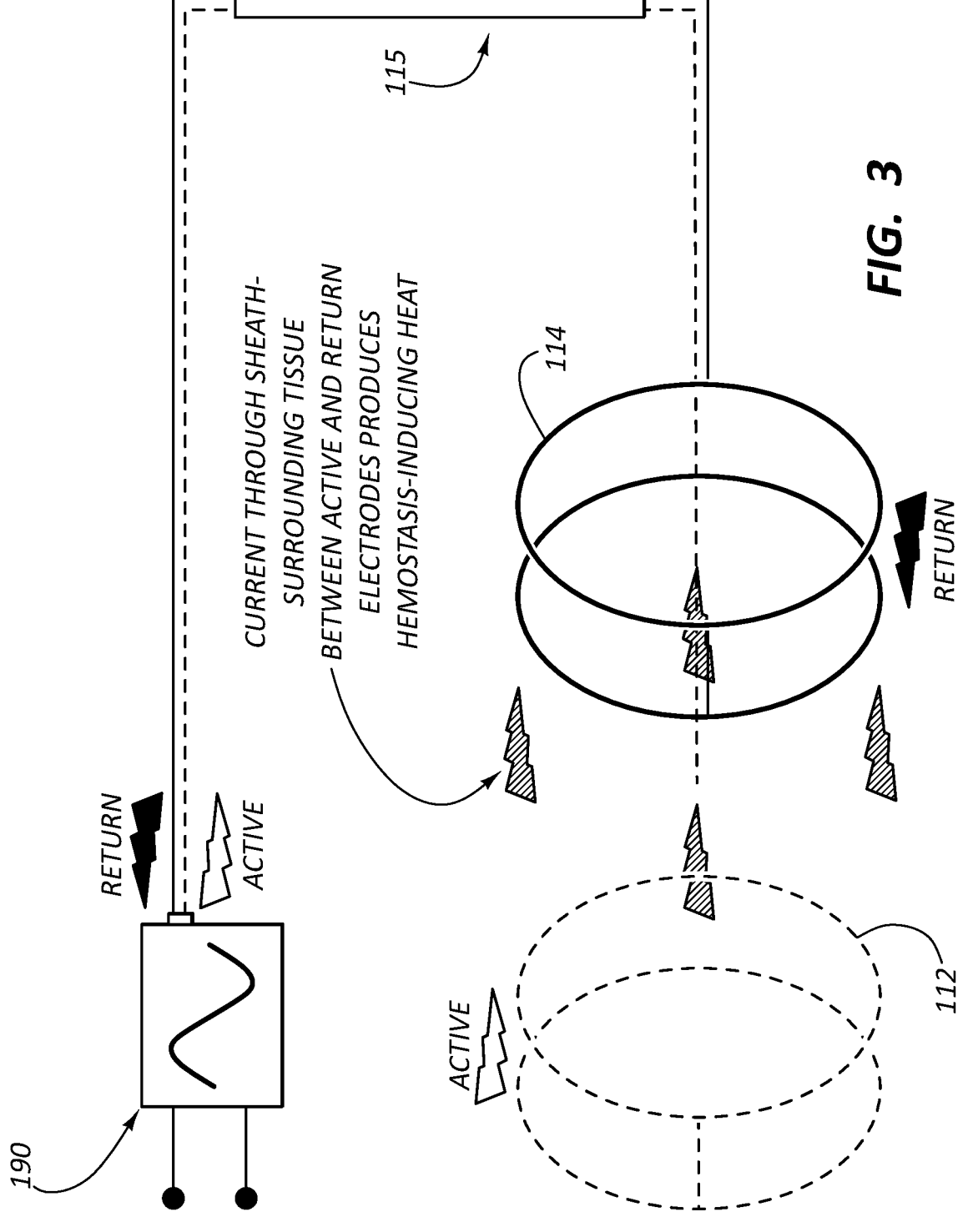

FIG. 3 provides a schematic illustrating an active electrode and a return electrode of a first electrode pair in accordance with some embodiments.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

PCNL is a minimally invasive surgical procedure primarily for removing kidney stones or other kidney obstructions from kidneys, wherein the stones or the other obstructions are either too large or too complex to be removed by other procedures. In a PCNL procedure, a puncture is made with a needle through a patient's back and into a kidney. Once a tract is established by the needle, the needle is replaced by a guidewire, a dilator is advanced over the guidewire to dilate the tract, and a renal sheath is advanced over the dilator. Removal of the dilator leaves the renal sheath, which provides a portal through which the PCNL procedure can be completed. However, the PCNL procedure is not without complications such as patient bleeding. As such, the PCNL procedure can benefit from mitigating or eliminating complications such as patient bleeding. Provided herein in some embodiments are systems and methods that address the foregoing, thereby reducing risk associated with the PCNL procedure.

For example, in some embodiments, a system is provided including a renal sheath, one or more electrode pairs in the renal sheath, and a wiring system configured to connect the one or more electrode pairs to an electric current. The renal sheath can include a distal end portion, a proximal end portion, and a medial portion between the distal and proximal end portions, the medial portion including the one or more electrode pairs disposed therein. The one or more electrode pairs can be configured to produce heat sufficient to induce hemostasis in bleeding tissue surrounding the renal sheath. The wiring system can be configured to connect the one or more electrode pairs to the electric current to produce the heat sufficient to effect the hemostasis.

FIGS. 1A and 1B provide schematics respectively illustrating a top view and a side view of a renal sheath 100 with one or more electrode pairs 110 in accordance with some embodiments. FIGS. 2A and 2B likewise respectively provide schematics illustrating a top view and a side view of the renal sheath 100 with the one or more electrode pairs 110 in accordance with some embodiments. FIG. 2C provides a schematic illustrating a perspective view of the renal sheath 100 with the one or more electrode pairs 110 in accordance with some embodiments.

As shown, the renal sheath 100 can include a distal end portion 102, a proximal end portion 104, and a medial portion 106, the medial portion including the one or more electrode pairs 110 disposed or embedded therein. Near a proximal end of the renal sheath 100, the renal sheath 100 can include a guidewire notch 105 configured to hold a guidewire in place therein. The proximal end portion 104 of the renal sheath 100 includes the proximal end or proximal terminus, in which the proximal end portion 104 of the renal sheath 100 terminates. The distal end portion 102 of the renal sheath 100 includes the distal end or distal terminus, in which the distal end portion 102 of the renal sheath 100 terminates. The distal end of the renal sheath 100 can be a beveled distal end 103 for atraumatic insertion of the renal sheath 100 into a dilated tract over a dilator.

The renal sheath 100 can be of any size convenient for a PCNL procedure. For example, the renal sheath 100 can be at least about 8 mm in diameter and 17 cm in length, 10 mm in diameter and 17 cm in length, or 10 mm in diameter and 22 cm in length for larger patients.

The renal sheath 100 can be one or more layers (e.g., two layers) of any biocompatible material or materials convenient for a PCNL procedure. For example, the renal sheath 100 can include poly(vinyl chloride) ("PVC"), polytetrafluoroethylene ("PTFE"), or a combination of PVC and PTFE. If PTFE or PVC, the renal sheath 100 can include 8-10% bismuth making the renal sheath 100 radiopaque for radiographic visualization. If PVC, the renal sheath 100 can include transparent PVC for enhanced visualization of surrounding tissue. If transparent PVC, a non-transparent marker band can be included in the renal sheath 100 for accurate insertion of the renal sheath 100 into a dilated tract over a dilator. The non-transparent marker band can be in the distal end portion 102 of the renal sheath 100 such as near or at the beveled distal end 103 of the renal sheath 100.

The renal sheath 100 can be of any biocompatible material or materials suitable for reusing the renal sheath 100 in a number of PCNL procedures. Such biocompatible material or materials include those that can be sterilized by chemical, physical (e.g., heat, pressure, etc.), or chemical and physical means in an adequate time period for meeting scheduling demands of the number of PCNL procedures.

One or more electrode pairs 110 can be disposed or embedded in the renal sheath 100, and the one or more electrode pairs 110 can be configured to produce heat sufficient to induce hemostasis in bleeding tissue surrounding the renal sheath 100. A first electrode pair is shown in the figures as an example of the one or more electrode pairs 110, the first electrode pair including a first electrode 112 and a second electrode 114. Each electrode pair of the one or more electrode pairs 110 can include an active electrode and a return electrode forming the electrode pair. For example, the first electrode 112 can be an active electrode, and the second electrode 114 can be a return electrode. As provided in reference to FIG. 3, the heat sufficient to effect the hemostasis can be produced in circuit-completing bleeding tissue surrounding the renal sheath between the active and return electrodes.

As further shown, the renal sheath can include a wiring system to connect the renal sheath 100 or the one or more electrode pairs 110 thereof to an electrical current such as an alternating electrical current. Diagrammatically, such a wiring system is shown in FIG. 3 for the renal sheath 100 including the first electrode pair with the first, active electrode 112 and the second, return electrode 114.

The wiring system can include a pair of wires at least partially disposed within a wall of the renal sheath 100 extending from a proximal end of the renal sheath 100 to at least the first electrode pair of the one or more electrode pairs 110. An active wire of the pair of wires can be connected to the first, active electrode 112 of the first electrode pair, and a return wire can be connected to the second, return electrode 114 of the first electrode pair 110. Distal to the first electrode pair of FIG. 3, additional electrode pairs such as a second electrode pair can be connected to the pair of wires. An active wire of the pair of wires can be connected to each of the active electrodes of the one or more electrode pairs 110, and a return wire can be connected to each of the return electrodes of the one or more electrode pairs 110. The additional electrode pairs such as the second electrode pairs can be connected, for example, in parallel with the first electrode pair to the pair of wires to maintain a certain voltage drop across each of the electrode pairs.

The wiring system can further include an external cable 115 including an external portion of the pair of wires extending from the proximal end of the renal sheath 100. The wiring system can further include a connector 116 at a proximal end of the external cable 115 opposite the renal sheath 110 configured to connect the renal sheath 100 or the one or more electrode pairs 110 thereof to the electrical current such as the alternating electrical current of an electrosurgical generator 190 (see FIG. 3).

Regarding placement of the external cable 115 on the renal sheath 100, the external cable 115 can be placed on one side of the renal sheath 100 to minimize a potential for interference with other components of the renal sheath 100. For example, the guidewire notch 105 can be in a wall of the renal sheath 100 opposite the wall of the renal sheath 100 including the pair of wires as shown in FIGS. 1B, 2A, and 2B. This serves to minimize a potential for interference between a guidewire in the guidewire notch 105 and the external cable 115.

FIG. 3 provides a schematic illustrating an active electrode and a return electrode of a first electrode pair in accordance with some embodiments.

As shown, a current-passing electrode pair of FIG. 3 is exemplified by the first, active electrode 112 electrically connected to the electrosurgical generator 190 by an active wire of the wiring system and the second, return electrode 114 electrically connected to the electrosurgical generator 190 by a return wire of the wiring system. When tissue such as bleeding tissue surrounding the renal sheath 100 is between the first, active electrode 112 and the second, return electrode 114, the tissue can complete a circuit between the first, active electrode 112 and the second, return electrode 114. Current (e.g., high-frequency electric current) passing from the first, active electrode 112 to the second, return electrode 114 through the circuit-completing tissue can produce sufficient heat in the tissue to induce hemostasis thereof.

In view of the foregoing, in some embodiments, the renal sheath can be a long (e.g., ≥17 cm) dual-layered PTFE tube with a chamfered distal end. The renal sheath can provide continuous access to a kidney during a PCNL procedure. As an alternative, the foregoing renal sheath can include a transparent PVC to allow for endoscopic visualization of tissue through the walls of the renal sheath. In either case, the electrohemostatic renal sheath can incorporate circumferential electrode pairs into a main body of the renal sheath, although use of the transparent PVC can offer an advantage by allowing visualization of the tissue in contact with the electrode pairs in order to confirm placement. With the renal sheath in place, a high-frequency low-voltage alternating current (e.g., radio frequency ["RF"] energy of about 3 kHz to 300 GHz) can be applied to the electrode pairs by a connected electrosurgical generator. The current can passes through the tissue in contact with the electrode pairs to complete the circuit, inducing hemostasis within the tract. The remainder of the PCNL procedure, including stone fragmentation and retrieval, is unchanged by the renal sheath device and can be performed in the accepted fashion.

In such embodiments, dual circumferential electrode pairs can be incorporated into a main body of the renal sheath such that outer surfaces of the electrode pairs are exposed and tangent to an outer diameter of the renal sheath, thereby allowing electrical contact between tissue surrounding the renal sheath and the electrode pairs while maintaining a smooth atraumatic outer surface. Wires can run within the walls of the renal sheath from a proximal end to the electrode pairs to carry the electrical current to each electrode. The wires can terminate in a connector for plugging the renal sheath into an electrosurgical generator to supply the electrical current.

Methods include making a puncture with a needle through a patient's back and into a kidney. Once a tract is established by the needle, the method further includes replacing the needle by a guidewire, advancing a dilator over the guidewire to dilate the tract, and advancing a renal sheath disclosed herein over the dilator. The method further includes removing the dilator and leaving the renal sheath, which provides a portal through which the PCNL procedure can be completed. Should any complications such as patient bleeding occur, the method further includes mitigating or eliminating the complications by producing heat with the renal sheath sufficient to effect the hemostasis.

As such, provided herein, in some embodiments, is a system including a renal sheath, one or more electrode pairs in the renal sheath, and a wiring system configured to connect the one or more electrode pairs to an electric current. The renal sheath can include a distal end portion, a proximal end portion, and a medial portion between the distal and proximal end portions, the medial portion including the one or more electrode pairs disposed therein. The one or more electrode pairs can be configured to produce heat sufficient to induce hemostasis in bleeding tissue surrounding the renal sheath. The wiring system can be configured to connect the one or more electrode pairs to the electric current to produce the heat sufficient to effect the hemostasis.

In such embodiments, the system can further include an electrosurgical generator configured to provide an alternating electric current to the one or more electrode pairs to produce the heat sufficient to effect the hemostasis.

In such embodiments, the one or more electrode pairs can be embedded in the renal sheath. Each electrode pair of the one or more electrode pairs can include an active electrode and a return electrode, wherein the heat sufficient to effect the hemostasis can be produced in circuit-completing bleeding tissue surrounding the renal sheath between the active and return electrodes.

In such embodiments, the wiring system can include a pair of wires at least partially disposed within a wall of the renal sheath extending from a proximal end of the renal sheath to at least a first electrode pair of the one or more electrode pairs.

In such embodiments, the system can further include a guidewire notch in the proximal end portion of the renal sheath. The guidewire notch can be in a wall of the renal sheath opposite the wall including the pair of wires.

In such embodiments, a distal end of the renal sheath can be beveled for atraumatic insertion of the renal sheath into a dilated tract over a dilator.

In such embodiments, the renal sheath can include PVC, PTFE, or a combination of PVC and PTFE.

In such embodiments, the renal sheath can include transparent PVC and a non-transparent marker band for accurate insertion of the renal sheath into a dilated tract over a dilator.

In such embodiments, the renal sheath can be at least about 8 mm in diameter and 17 cm in length, 10 mm in diameter and 17 cm in length, or 10 mm in diameter and 22 cm in length for larger patients.

Also provided herein, in some embodiments, is a system including a renal sheath, one or more electrode pairs in the renal sheath, a wiring system configured to connect the one or more electrode pairs to an alternating electric current, and an electrosurgical generator configured to provide the alternating electric current. The renal sheath can include a distal end portion, a proximal end portion, and a medial portion between the distal and proximal end portions, the medial portion including the one or more electrode pairs disposed therein. The one or more electrode pairs can be configured to produce heat sufficient to induce hemostasis in bleeding tissue surrounding the renal sheath. The wiring system can be configured to connect the one or more electrode pairs to the electrosurgical generator-provided alternating electric current to produce the heat sufficient to effect the hemostasis.

In such embodiments, the one or more electrode pairs can be embedded in the renal sheath. Each electrode pair of the one or more electrode pairs can include an active electrode and a return electrode, wherein the heat sufficient to effect the hemostasis can be produced in circuit-completing bleeding tissue surrounding the renal sheath between the active and return electrodes.

In such embodiments, the wiring system can include a pair of wires at least partially disposed within a wall of the renal sheath extending from a proximal end of the renal sheath to at least a first electrode pair of the one or more electrode pairs. The wiring system can further include an external cable including an external portion of the pair of wires extending from the proximal end of the renal sheath. The wiring system can further include a connector at a proximal end of the external cable opposite the renal sheath configured to connect the renal sheath to the electrosurgical generator.

In such embodiments, the system can further include a guidewire notch in the proximal end portion of the renal sheath. The guidewire notch can be in a wall of the renal sheath opposite the wall including the pair of wires to minimize a potential for interference between a guidewire in the guidewire notch and the external cable.

In such embodiments, a distal end of the renal sheath can be beveled for atraumatic insertion of the renal sheath into a dilated tract over a dilator.

In such embodiments, the renal sheath can include PVC, PTFE, or a combination of PVC and PTFE.

In such embodiments, the renal sheath can include transparent PVC and a non-transparent marker band for accurate insertion of the renal sheath into a dilated tract over a dilator.

In such embodiments, the renal sheath can be at least about 8 mm in diameter and 17 cm in length, 10 mm in diameter and 17 cm in length, or 10 mm in diameter and 22 cm in length for larger patients.

Also provided herein, in some embodiments, is a system including a renal sheath, at least two electrode pairs embedded in the renal sheath, and a wiring system configured to connect the at least two electrode pairs to an alternating electric current. The renal sheath can include a distal end portion, a proximal end portion, and a medial portion between the distal and proximal end portions, the medial portion including the at least two electrode pairs embedded therein. Each electrode pair of the at least two electrode pairs can include an active electrode and a return electrode. The at least two electrode pairs can be configured to produce heat sufficient to induce hemostasis in circuit-completing bleeding tissue surrounding the renal sheath between the active and return electrodes. The wiring system can be configured to connect the at least two electrode pairs to the alternating electric current to produce the heat sufficient to effect the hemostasis. The wiring system can include a pair of wires at least partially disposed within a wall of the renal sheath extending from a proximal end of the renal sheath to a first electrode pair of the at least two electrode pairs. The wiring system can further include an external cable including an external portion of the pair of wires extending from the proximal end of the renal sheath. The wiring system can further include a connector at a proximal end of the external cable opposite the renal sheath configured to connect the renal sheath to an electrosurgical generator.

In such embodiments, the system can further include a guidewire notch in the proximal end portion of the renal sheath. The guidewire notch can be in a wall of the renal sheath opposite the wall including the pair of wires to minimize a potential for interference between a guidewire in the guidewire notch and the external cable. In addition, a distal end of the renal sheath can be beveled for atraumatic insertion of the renal sheath into a dilated tract over a dilator.

In such embodiments, the renal sheath can includes polytetrafluoroethylene or transparent poly(vinyl chloride) with a non-transparent marker band for accurate insertion of the renal sheath into a dilated tract over a dilator.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:
1. A system, comprising:
a renal sheath including:
a distal end portion, a proximal end portion, and a medial portion between the distal end portion and the proximal end portion, the renal sheath configured to provide a portal for kidney-stone fragmentation and retrieval during a percutaneous nephrolithotomy procedure; and
one or more electrode pairs disposed in the medial portion of the renal sheath, the one or more electrode pairs designed to produce heat sufficient to induce hemostasis in bleeding tissue surrounding the renal sheath;
a wiring system designed to connect the one or more electrode pairs to an electric current to produce the heat sufficient to induce the hemostasis;
a needle configured to establish a needle tract from a back to a kidney of a patient; and
a dilator configured to dilate the needle tract to establish a dilated tract, wherein a distal end of the renal sheath is beveled for atraumatic insertion of the renal sheath into the dilated tract over the dilator.
2. The system according to claim 1, further comprising an electrosurgical generator designed to provide an alternating electric current to the one or more electrode pairs to produce the heat sufficient to induce the hemostasis.
3. The system according to claim 1, wherein:
the one or more electrode pairs are embedded in the renal sheath, each electrode pair of the one or more electrode pairs includes an active electrode and a return electrode, and the heat sufficient to induce the hemostasis is produced in circuit-completing bleeding tissue surrounding the renal sheath between the active electrode and the return electrode.

4. The system according to claim 1, wherein the wiring system includes a pair of wires at least partially disposed within a first wall of the renal sheath extending from a proximal end of the renal sheath to at least a first electrode pair of the one or more electrode pairs.

5. The system according to claim 4, further comprising a guidewire notch in the proximal end portion of the renal sheath, wherein the guidewire notch is in a second wall of the renal sheath opposite the first wall including the pair of wires.

6. The system according to claim 1, wherein the renal sheath includes poly(vinyl chloride) ("PVC"), polytetrafluoroethylene ("PTFE"), or a combination of PVC and PTFE.

7. The system according to claim 1, wherein the renal sheath includes transparent PVC and a non-transparent marker band for accurate insertion of the renal sheath into the dilated tract over the dilator.

8. The system according to claim 1, wherein the renal sheath is at least about 8 mm in diameter and 17 cm in length.

* * * * *